US012672846B2

(12) United States Patent
Torisawa et al.

(10) Patent No.: US 12,672,846 B2
(45) Date of Patent: Jul. 7, 2026

(54) ULTRASOUND PROBE WITH ILLUMINATION MEANS FOR LOCATING NEEDLE GUIDE HOLE

(71) Applicant: FUJIFILM Corporation, Tokyo (JP)

(72) Inventors: Nobuyuki Torisawa, Ashigarakami-gun (JP); Wataru Inoue, Ashigarakami-gun (JP); Satoshi Naito, Ashigarakami-gun (JP); Yukio Haga, Ashigarakami-gun (JP); Shozo Iyama, Ashigarakami-gun (JP)

(73) Assignee: FUJIFILM Corporation, Tokyo (JP)

( * ) Notice: Subject to any disclaimer, the term of this patent is extended or adjusted under 35 U.S.C. 154(b) by 0 days.

(21) Appl. No.: 18/796,307

(22) Filed: Aug. 7, 2024

(65) Prior Publication Data

US 2025/0099072 A1      Mar. 27, 2025

(30) Foreign Application Priority Data

Sep. 27, 2023    (JP) ................................. 2023-165284

(51) Int. Cl.
| | |
|---|---|
| *A61B 8/12* | (2006.01) |
| *A61B 5/00* | (2006.01) |
| *A61B 8/00* | (2006.01) |
| *A61B 90/00* | (2016.01) |

(52) U.S. Cl.
CPC .............. *A61B 8/12* (2013.01); *A61B 5/0093* (2013.01); *A61B 5/0095* (2013.01); *A61B 5/0097* (2013.01); *A61B 8/4444* (2013.01); *A61B 90/08* (2016.02)

(58) Field of Classification Search
CPC .............................. A61B 8/12; A61B 17/3403
See application file for complete search history.

(56) References Cited

U.S. PATENT DOCUMENTS

| | | | |
|---|---|---|---|
| 2017/0065250 A1* | 3/2017 | Sasady .................. | A61B 8/085 |
| 2022/0151707 A1* | 5/2022 | Sasaki .................. | A61B 8/445 |
| 2024/0173049 A1* | 5/2024 | Takeda .............. | A61B 17/3403 |

FOREIGN PATENT DOCUMENTS

| | | |
|---|---|---|
| CN | 215273179 | 12/2021 |
| JP | 2002191602 | 7/2002 |
| JP | 2024078826 | 6/2024 |
| WO | 2015166302 | 11/2015 |

OTHER PUBLICATIONS

"Search Report of Europe Counterpart Application", issued on Jan. 3, 2025, p. 1-p. 8.

* cited by examiner

*Primary Examiner* — Keith M Raymond
*Assistant Examiner* — Ashish S. Jasani
(74) *Attorney, Agent, or Firm* — JCIPRNET

(57)      ABSTRACT

An ultrasound probe includes: a distal end part that is provided with an ultrasound oscillator; and a light emitting unit that is provided at the distal end part and that emits light toward an opposite side to a side where the ultrasound oscillator is provided. The light emitting unit emits a plurality of point-like light beams or linear light.

19 Claims, 12 Drawing Sheets

VO

432La

P

Y1(Y)

X1(X) ←→ X2(X)

Y2(Y)

432La 432A    432a    432B    40

432Bs

ULTRASOUND PROBE WITH ILLUMINATION MEANS FOR LOCATING NEEDLE GUIDE HOLE

CROSS-REFERENCE TO RELATED APPLICATIONS

This application is based on and claims priority under 35 USC 119 from Japanese Patent Application No. 2023-165284 filed on Sep. 27, 2023, the contents of which are incorporated herein by reference.

BACKGROUND OF THE INVENTION

1. Field of the Invention

The present disclosed technology relates to an ultrasound probe.

2. Description of the Related Art

WO2015/166302A describes an ultrasound probe that radiates a light beam to an inner wall of a body cavity of a subject in an opposite direction of a conversion surface of a transducer array from a light source disposed adjacent to the transducer array.

JP2002-191602A describes an ultrasound probe for endoscope surgery having a slender and elongated body part that is inserted into a trocar tube inserted into an abdominal wall of a patient, a bending part that is attached to a distal end part of the body part, a head part that is attached to a distal end part of the bending part and that has an ultrasound oscillator at a distal end, a beam emitting unit that is provided at the head part and that irradiates the abdominal wall with a beam from the head part, and a guide unit that is provided at the head part and that guides a puncture needle.

SUMMARY OF THE INVENTION

The present disclosure provides a technique that can easily recognize a disposition state of the ultrasound probe in the subject.

According to the present disclosed technology, there is provided an ultrasound probe comprising a distal end part that is provided with an ultrasound oscillator and a light emitting unit that is provided at the distal end part and that emits light toward an opposite side to a side where the ultrasound oscillator is provided, in which the light emitting unit emits a plurality of point-like light beams or linear light.

With the present disclosed technology, it is possible to easily recognize a disposition state in a subject.

DESCRIPTION OF THE PREFERRED EMBODIMENTS

Figure 1:
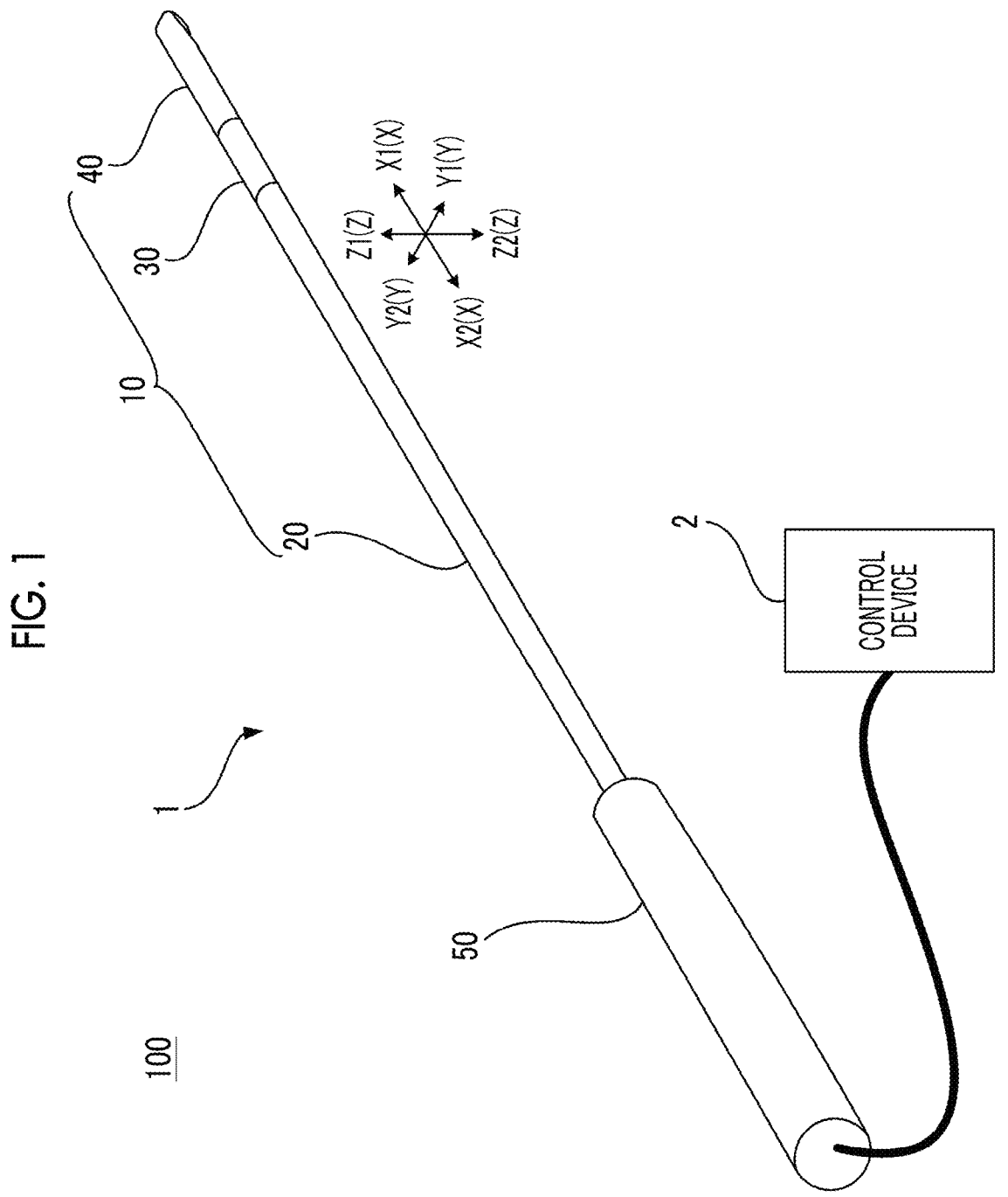
FIG. 1 is a schematic view showing a schematic configuration of an ultrasound diagnostic apparatus 100 that is an embodiment of the present disclosed technology.

FIG. 1 is a schematic view showing a schematic configuration of an ultrasound diagnostic apparatus 100 that is an embodiment of the present disclosed technology. The ultrasound diagnostic apparatus 100 comprises an ultrasound probe 1 and a control device 2 that is mainly composed of a processor which performs control of the ultrasound probe 1, generation of an ultrasound image, and the like based on an output of the ultrasound probe 1.

The ultrasound probe 1 is used by being introduced into an abdominal cavity through one of a plurality of trocars that have punctured an abdomen of a subject such as a person or an animal. While observing a state of the inside of the abdominal cavity with an endoscope introduced into a body cavity by another trocar among the plurality of trocars, a user operates the ultrasound probe 1 with the hand and closely attaches an ultrasound transmission/reception unit to a target examination part to obtain an ultrasound observation image, performing an examination.

The ultrasound probe 1 comprises a long columnar insertion part 10 to be inserted into the abdominal cavity and an operating part 50 to be gripped by the user. FIG. 1 shows a direction X1 from a proximal end toward a distal end of the insertion part 10 and a direction X2 that is an opposite direction of the direction X1 as an axial direction X of the insertion part 10. FIG. 1 shows a direction Y and a direction Z that intersect the axial direction X and that intersect each other. In the example of FIG. 1, each of the direction Y and the direction Z is orthogonal to the axial direction X. In addition, the direction Y and the direction Z are orthogonal to each other. One direction Y will be referred to as a direction Y1, and the other direction Y will be referred to as a direction Y2. One direction Z will be referred to as a direction Z1, and the other direction Y will be referred to as a direction Z2.

The insertion part 10 comprises a distal end part 40, a bendable part 30 that is provided at a proximal end of the distal end part 40, and a connecting portion 20 that connects the bendable part 30 to the operating part 50. The bendable part 30 is configured to have a sufficiently low stiffness compared to the connecting portion 20 and the distal end part 40 and is configured to be bendable in two directions intersecting each other (for example, the direction Y and the direction Z) with a wire or the like connected to a bendable operator (not shown) provided in the operating part 50 by operating the bendable operator. The bendable part 30 is not limited to a part that can be bent by operating the bendable operator and may be configured to be passively bent, for example, in a case where the distal end part 40 is pressed against the examination part.

Figure 2:
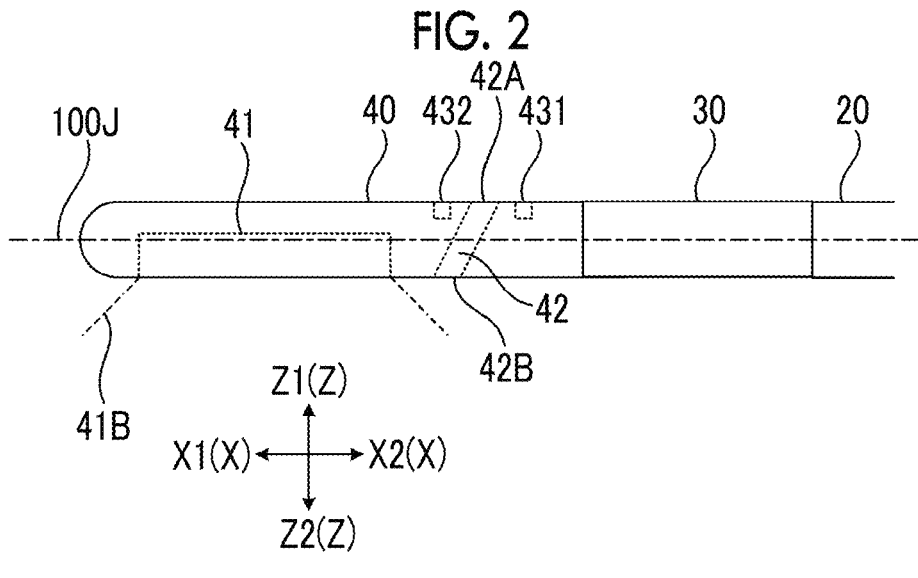
FIG. 2 is a side view of an insertion part 10 of the ultrasound probe 1 shown in FIG. 1 as viewed in a direction Y1.
Figure 3:
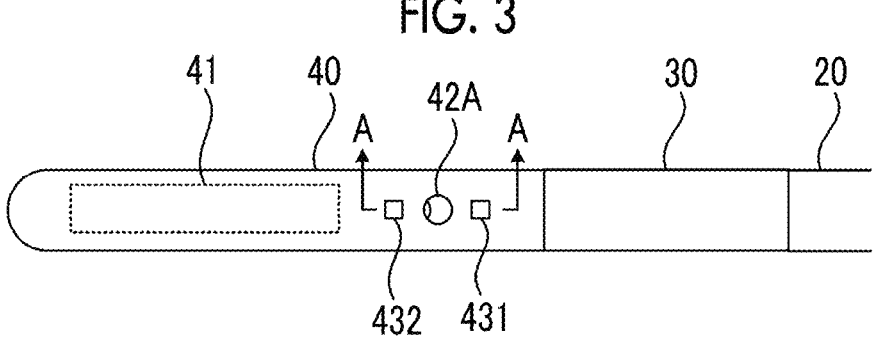
FIG. 3 is a bottom view of the insertion part 10 of the ultrasound probe 1 shown in FIG. 2 as viewed in a direction Z2.
Figure 3:
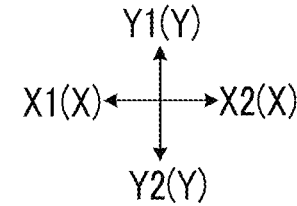
Figure 4:
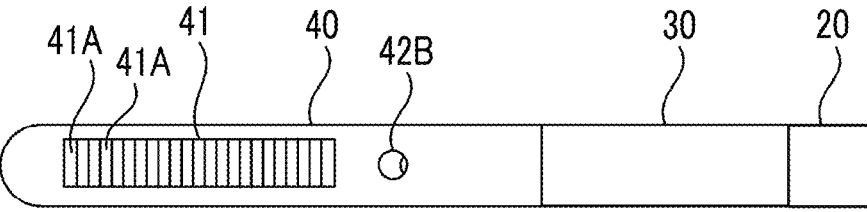
FIG. 4 is a plan view of the insertion part 10 of the ultrasound probe 1 shown in FIG. 2 as viewed in a direction Z1.
Figures 5, 6:
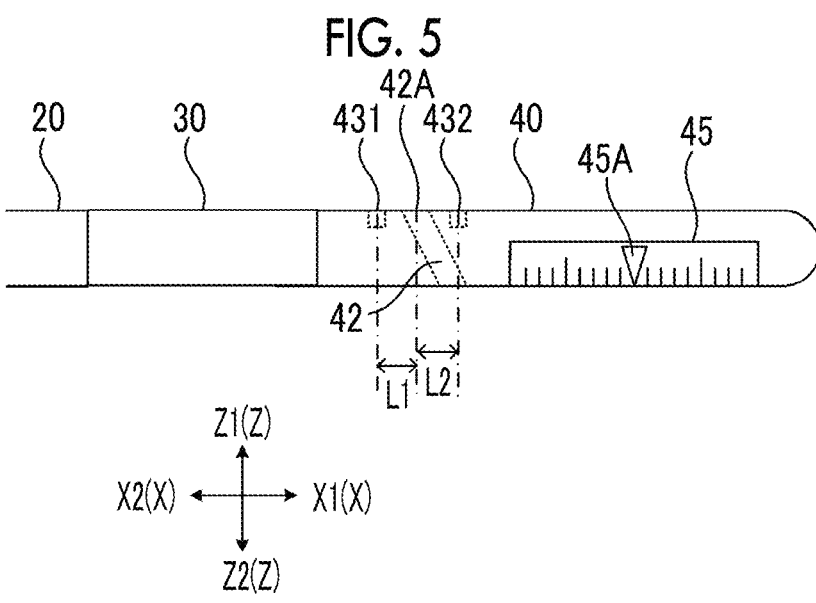
FIG. 5 is a side view of the insertion part 10 of the ultrasound probe 1 shown in FIG. 1 as viewed in a direction Y2.
FIG. 6 is a schematic cross-sectional view taken along line A-A of FIG. 3.

FIG. 2 is a side view of the insertion part 10 of the ultrasound probe 1 shown in FIG. 1 as viewed in the direction Y1. FIG. 3 is a bottom view of the insertion part 10 of the ultrasound probe 1 shown in FIG. 2 as viewed in the direction Z2. FIG. 4 is a plan view of the insertion part 10 of the ultrasound probe 1 shown in FIG. 2 as viewed in the direction Z1. FIG. 5 is a side view of the insertion part 10 of the ultrasound probe 1 shown in FIG. 1 as viewed in the direction Y2. FIG. 6 is a schematic cross-sectional view taken along line A-A of FIG. 3.

FIG. 2 shows an axial line 100J of the insertion part 10. The distal end part 40 is provided with an ultrasound transmission/reception unit 41, a guide unit 42 that guides a treatment tool such as a puncture needle, a first light emitting unit 431, and a second light emitting unit 432. Hereinafter, the treatment tool will be described as the puncture needle, but the present invention is not limited thereto.

The ultrasound transmission/reception unit 41 is provided on a surface of the distal end part 40 on a direction Z2 side and transmits ultrasound waves toward the direction Z2 side with respect to the axial line 100J in side view shown in FIG. 2. As shown in FIG. 4, the ultrasound transmission/reception unit 41 includes a plurality of ultrasound oscillators 41A arranged in the axial direction X, an acoustic matching layer, an acoustic lens, and the like (not shown). The shape of the ultrasound oscillator 41A viewed in an oscillation direction thereof is, for example, a rectangular shape. The ultrasound oscillator 41A is provided at the distal end part 40, for example, in a state where a longitudinal direction thereof extends along the direction Y.

As shown in FIG. 5, a scale 45 is provided on a surface of the distal end part 40 on a direction Y1 side. The scale 45 includes a mark 45A indicating the center of the ultrasound transmission/reception unit 41 in the axial direction X. With reference to the scale 45, it is possible to learn a correspondence relationship between a scan range 41B of ultrasound waves from the ultrasound transmission/reception unit 41 (a part observed in an ultrasound image, see FIG. 2) and the ultrasound image. The scale 45 may be provided on a surface of the distal end part 40 on a direction Y2 side.

As shown in FIG. 6, the guide unit 42 guides the treatment tool (puncture needle) to the scan range 41B of ultrasound waves, and the guide unit 42 is used so that the puncture needle can accurately puncture a puncture target. Specifically, the guide unit 42 is composed of a hole portion that connects, for example, a circular opening 42A provided in a surface on a direction Z1 side and, for example, a circular opening 42B provided in a surface on the direction Z2 side. The guide unit 42 is provided between the ultrasound transmission/reception unit 41 and the bendable part 30. In the axial direction X, the opening 42B is disposed on a direction X1 side of the opening 42A. That is, an extension line 42J of an axial line of the guide unit 42 is inclined to a direction X2 side with respect to the direction Z. In a state where the ultrasound transmission/reception unit 41 is pressed against an organ or the like of the subject, the treatment tool (puncture needle) is inserted into the guide unit 42 from the opening 42A, so that a distal end of the treatment tool can reach the scan range 41B of ultrasound waves from the ultrasound transmission/reception unit 41. The extension line 42J extends in a direction along an inner wall surface of the guide unit 42 and in the example of FIG. 6, is parallel to the inner wall surface (an inner wall surface 421 on the direction X1 side and an inner wall surface 422 on the direction X2 side).

The first light emitting unit 431 and the second light emitting unit 432 are provided on a surface of the distal end part 40 on the direction Z1 side and emit light toward the direction Z1 side of the axial line 100J. In the distal end part 40, a side where the ultrasound oscillators 41A are provided is configured as the direction Z2 side of the axial line 100J, and each of the first light emitting unit 431 and the second light emitting unit 432 emits light toward an opposite side to the side where the ultrasound oscillators 41A are provided.

As shown in FIG. 3, the first light emitting unit 431 and the second light emitting unit 432 are arranged in the axial direction X and are provided at positions facing each other with the guide unit 42 interposed therebetween. The first light emitting unit 431 includes a recessed portion 431a provided in the surface of the distal end part 40 on the direction Z1 side and a light source 431A provided in the recessed portion 431a. The second light emitting unit 432 includes a recessed portion 432a provided in the surface of the distal end part 40 on the direction Z1 side and a light source 432A provided in the recessed portion 432a. The second light emitting unit 432 is provided on a distal end side (direction X1 side) of the distal end part 40 with respect to the first light emitting unit 431. A first distance L1 between the first light emitting unit 431 and the guide unit 42 (defined as a distance between an opening center of the recessed portion 431a and a center of the opening 42A in the axial direction X) and a second distance L2 between the second light emitting unit 432 and the guide unit 42 (defined as a distance between an opening center of the recessed portion 432*a* and the center of the opening 42A in the axial direction X) are the same but may be different from each other.

The light source 432A emits point-like light 432L that travels in a direction in which the extension line 42J extends (the same as a direction along the inner wall surface 421). The light source 431A emits point-like light 431L that travels in a direction in which the extension line 42J extends (the same as a direction along the inner wall surface 422). As each of the light source 431A and the light source 432A, a xenon lamp or the like can be used by interposing a light guide path, in addition to a light emitting element such as a laser, a light emitting diode (LED), an organic electro-luminescence (EL), and an inorganic EL. Although not particularly limited, it is preferable to use a laser from the viewpoint of visibility. The first light emitting unit 431 and the second light emitting unit 432 may further include an optical member or the like for improving the straightness of light from the light source or controlling a traveling direction.

An abdominal wall is irradiated from the abdominal cavity of the subject with light emitted from the first light emitting unit 431 and the second light emitting unit 432. However, herein, a case where an imaginary plane VO perpendicular to the direction Z is irradiated with the light will be described in order to describe an irradiation state of the light from the distal end part 40 to the subject. The imaginary plane VO corresponds to the abdominal wall of the subject. As shown in FIG. 6, the imaginary plane VO is disposed on the direction Z1 side of the distal end part 40.

Figures 7, 8:
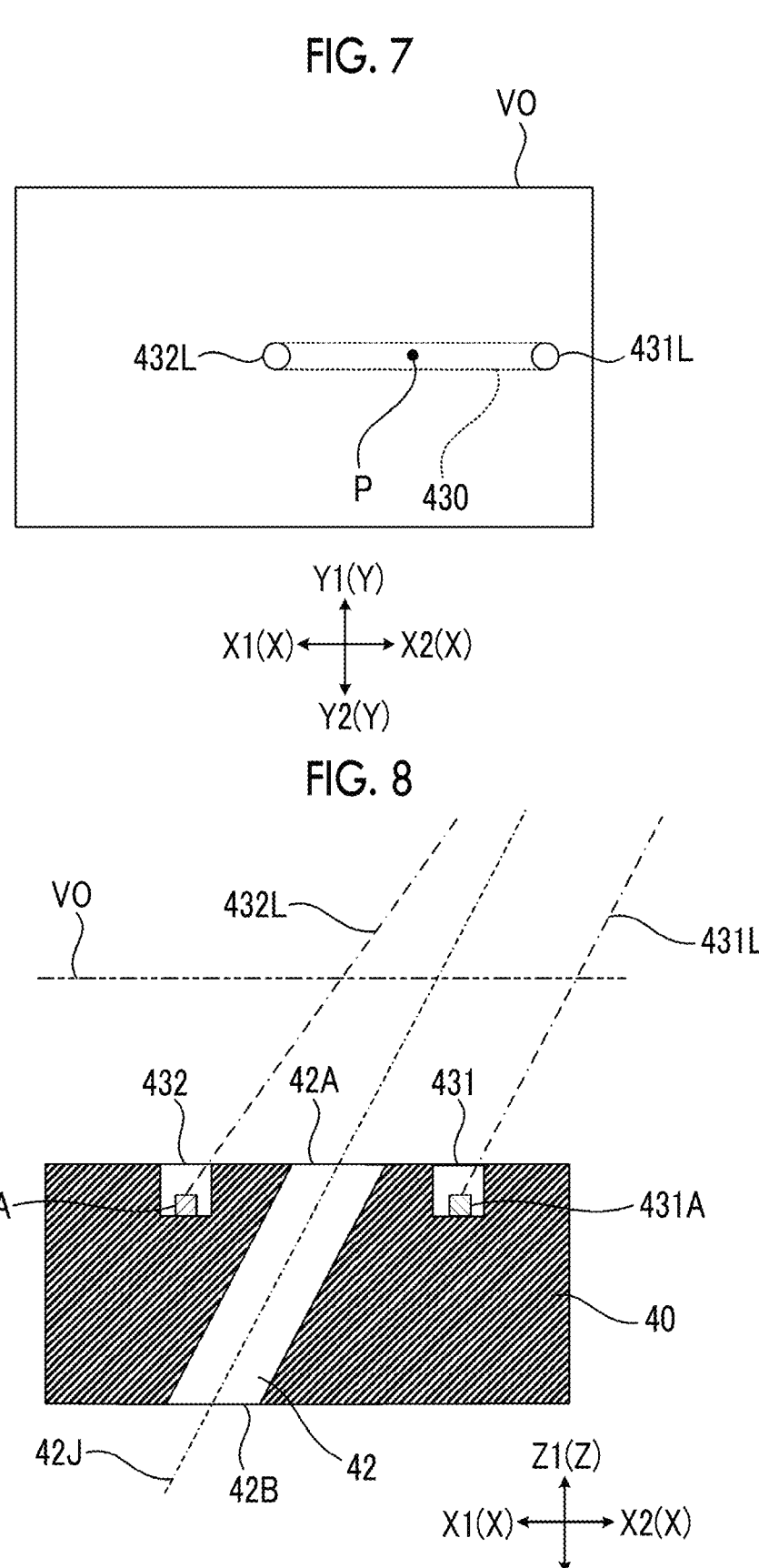
FIG. 7 is a view of an imaginary plane VO as viewed in the direction Z2.
FIG. 8 is a view showing a modification example of a cross section taken along the line A-A of FIG. 3.

FIG. 7 is a view of the imaginary plane VO as viewed in the direction Z2. The imaginary plane VO is irradiated with the point-like light 432L and the point-like light 431L in a state of being arranged at an interval along the axial direction X (the same as an arrangement direction of the ultrasound oscillators 41A). As described above, the first light emitting unit 431 and the second light emitting unit 432 emit the point-like light 432L and the point-like light 431L based on the arrangement of the ultrasound oscillators 41A. In addition, since the light 432L and the light 431L are emitted in directions along the inner wall surface 421 and the inner wall surface 422 of the guide unit 42, and it can be said that the light 432L and the light 431L are emitted based on the shape of the guide unit 42. That is, the first light emitting unit 431 and the second light emitting unit 432 emit the point-like light 432L and the point-like light 431L based on the shape of the guide unit 42.

In the imaginary plane VO, a range between the light 432L and the light 431L is defined as an irradiation range 430 of the light. An intersection P with the extension line 42J in the imaginary plane VO overlaps the irradiation range 430. The intersection P is positioned at the center of the irradiation range 430 in the axial direction X.

The irradiation range 430 corresponds to a range obtained by parallel-moving a region of the surface of the distal end part 40 on the direction Z1 side, in which the second light emitting unit 432, the opening 42A, and the first light emitting unit 431 are provided, in the direction Z1 along the extension line 42J. Therefore, by inserting the treatment tool obliquely with respect to the substantially center of the irradiation range 430, it is easy to insert the treatment tool into the guide unit 42.

With the ultrasound probe 1 configured as described above, the puncture needle easily reaches the guide unit 42 by inserting the puncture needle obliquely with respect to the abdomen in a state where a proximal end side of the puncture needle is tilted to a light 431L side by targeting an approximate center of the irradiation range 430 surrounded by the light 431L and the light 432L with the light 431L and the light 432L emitted from the inside of the abdominal cavity of the subject to the abdominal wall as a guide. For example, in a configuration where the abdominal wall is irradiated with only one beam of the light 431L and the light 432L, it is difficult to learn in which direction the guide unit 42 is positioned with respect to the emitted light, and it is difficult to determine in which direction the puncture needle needs to puncture with respect to the emitted light. On the other hand, with the ultrasound probe 1, since a direction in which the light 431L and the light 432L are arranged can be recognized as a puncture direction of the puncture needle, it is possible to efficiently perform the puncture by the puncture needle with respect to a part against which the ultrasound transmission/reception unit 41 is pressed. In addition, by inserting the puncture needle into the guide unit 42, the puncture needle can accurately puncture a target part in the scan range of ultrasound waves that can be recognized in an ultrasound image.

In addition, in a case where the first distance L1 between the first light emitting unit 431 and the opening 42A and the second distance L2 between the second light emitting unit 432 and the opening 42A are the same, as shown in FIG. 7, the intersection P is positioned at the center of the irradiation range 430. Therefore, it is possible to more easily recognize an insertion position of the treatment tool with respect to the irradiation range 430.

In order to easily recognize in which direction the guide unit 42 is present with respect to the irradiation range 430 or in order to easily recognize which of the light 432L and the light 431L is present at a position closer to the ultrasound transmission/reception unit 41, light emission forms may be different between the light 432L and the light 431L. For example, colors of the light 432L and the light 431L may be different from each other, irradiation sizes of the light 432L and the light 431L in the imaginary plane VO may be different from each other, the brightness of the light 432L and the brightness of the light 431L may be different from each other, or the light 432L and the light 431L may have different light emission periods (light emission in an inter-mittent manner, light emission in a continuous manner, and the like). The fact that the irradiation sizes of the light 432L and the light 431L in the imaginary plane VO are different from each other means that the irradiation sizes of the light 432L and the light 431L are non-uniform.

FIG. 8 is a view showing a modification example of the cross section taken along the line A-A of FIG. 3. The modification example shown in FIG. 8 is the same as FIG. 3 except that an emission direction of the light 432L is inclined to the extension line 42J side with respect to the direction in which the extension line 42J extends. In FIG. 8, the emission direction of the light 431L may be inclined to the extension line 42J side with respect to the direction in which the extension line 42J extends. In addition, the emission direction of the light 432L may be the same as the direction in which the extension line 42J extends, and the emission direction of the light 431L may be inclined to the extension line 42J side with respect to the direction in which the extension line 42J extends. Even with these configurations, a direction of insertion of the treatment tool can be recognized by the irradiation range 430. In addition, since the width of the irradiation range 430 is narrowed, it is possible to suppress the blur of the insertion position of the treatment tool.

Figures 9, 10, 11:
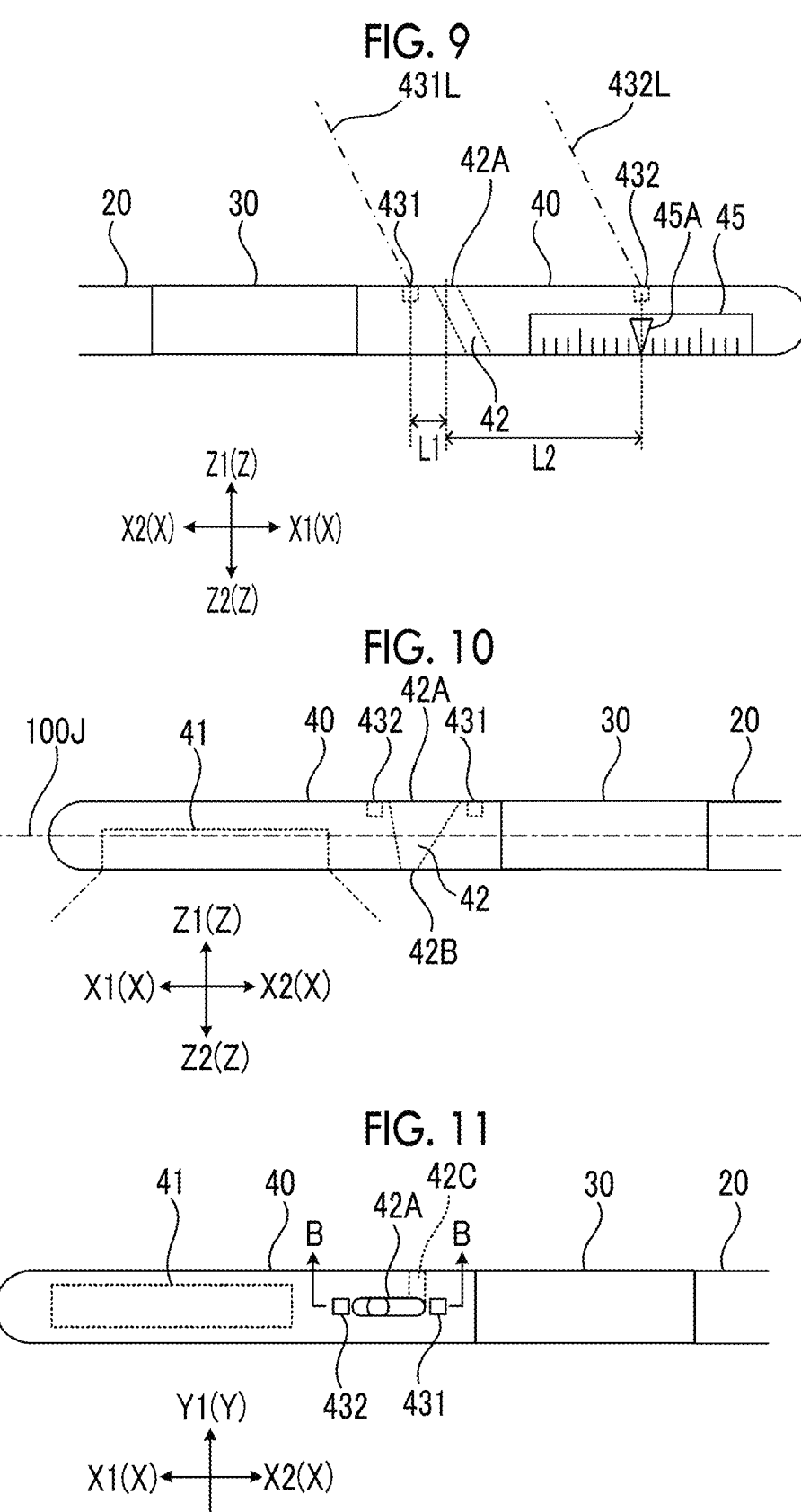
FIG. 9 is a view for describing a first modification example of a distal end part 40 and is a view corresponding to FIG. 5.
FIG. 10 is a view for describing a second modification example of the distal end part 40 and is a view corresponding to FIG. 2.
FIG. 11 is a view of the ultrasound probe 1 shown in FIG. 10 as viewed in the direction Z2.

FIG. 9 is a view for describing a first modification example of the distal end part 40 and is a view corresponding to FIG. 5. The distal end part 40 of the first modification example has the same configuration as that of the distal end part 40 shown in FIGS. 2 to 5, except that the position of the second light emitting unit 432 is changed to the same position as that of the mark 45A in the axial direction X. In the distal end part 40 shown in FIG. 9, the second distance L2 between the second light emitting unit 432 and the guide unit 42 is larger than the first distance L1 between the first light emitting unit 431 and the guide unit 42.

With the configuration shown in FIG. 9, the abdominal wall is irradiated with the light 431L corresponding to a position in the vicinity of the guide unit 42 and the light 432L corresponding to the position of the mark 45A. Accordingly, with reference to the light 432L, it is possible to easily recognize where the center position of an ultrasound image is. With reference to the light 431L, it is possible to easily recognize where the guide unit 42 is. For example, even in a case where it is desired to insert the treatment tool at a position different from the position of the guide unit 42, the treatment tool can be easily inserted at a target position as the center of the ultrasound image can be recognized.

Figure 12:
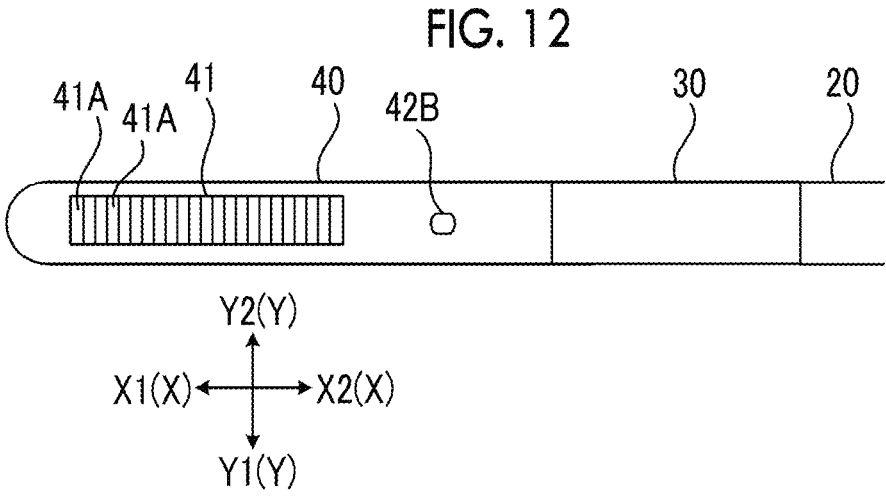
FIG. 12 is a view of the ultrasound probe 1 shown in FIG. 10 as viewed in the direction Z1.
Figure 13:
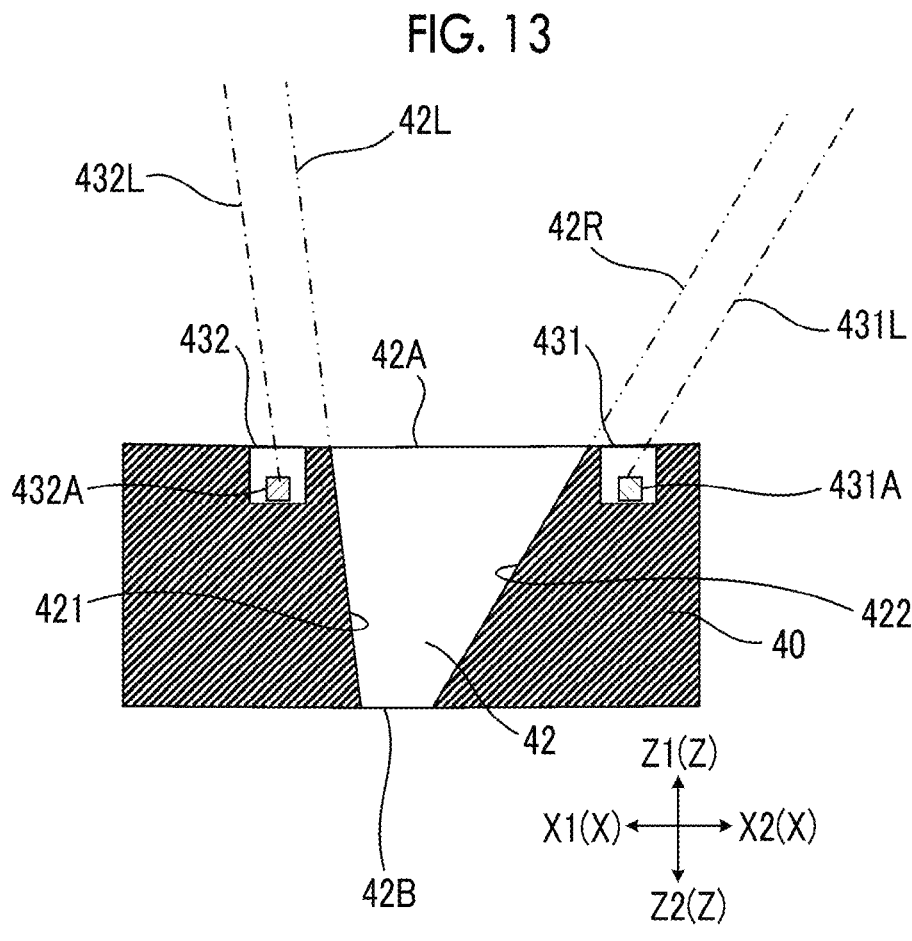
FIG. 13 is a schematic cross-sectional view taken along line B-B of FIG. 11.

FIG. 10 is a view for describing a second modification example of the distal end part 40 and is a view corresponding to FIG. 2. FIG. 11 is a view of the ultrasound probe 1 shown in FIG. 10 as viewed in the direction Z2. FIG. 12 is a view of the ultrasound probe 1 shown in FIG. 10 as viewed in the direction Z1. FIG. 13 is a schematic cross-sectional view taken along line B-B of FIG. 11.

The distal end part 40 shown in FIGS. 10 to 12 has the same configuration as that of the distal end part 40 shown in FIGS. 2 to 5, except that the shape of the guide unit 42 is different and emission directions of light of the first light emitting unit 431 and the second light emitting unit 432 are different.

As shown in FIG. 11, the opening 42A has an elliptical shape extending in the axial direction X. As shown in FIG. 12, the opening 42B has an elliptical shape extending in the axial direction X, but has a shorter length than the opening 42A. As shown in FIG. 13, the cross-sectional shape of the guide unit 42 is a tapered shape in which an inner diameter increases from the direction Z2 toward the direction Z1. In the cross section shown in FIG. 13, the inner wall surface 421 of the guide unit 42 on the direction X1 side is inclined to the direction X1 side with respect to the direction Z, and the inner wall surface 422 of the guide unit 42 on the direction X2 side is inclined to the direction X2 side with respect to the direction Z. For example, as shown in FIG. 11, a through-hole 42C that extends to the guide unit 42 may be provided in the surface of the distal end part 40 on the direction Y1 side.

The light source 432A shown in FIG. 13 emits the point-like light 432L that travels in the direction along the inner wall surface 421. FIG. 13 shows an extension line 42L of the inner wall surface 421, and the light 432L is parallel to the extension line 42L. The light source 431A shown in FIG. 13 emits the point-like light 431L that travels in the direction along the inner wall surface 422. FIG. 13 shows an extension line 42R of the inner wall surface 422, and the light 431L is parallel to the extension line 42R.

By using the guide unit 42 having such a configuration, it is possible to insert the treatment tool at an angle along the inner wall surface 421 or to insert the treatment tool at an angle along the inner wall surface 422. Even with such a configuration of the guide unit 42, the treatment tool can be easily inserted into the guide unit 42 at different angles by inserting the treatment tool at a position in the vicinity of the light 432L in the irradiation range 430 at the angle along the inner wall surface 421 or inserting the treatment tool at a position in the vicinity of the light 431L in the irradiation range 430 at the angle along the inner wall surface 422.

Figure 14:
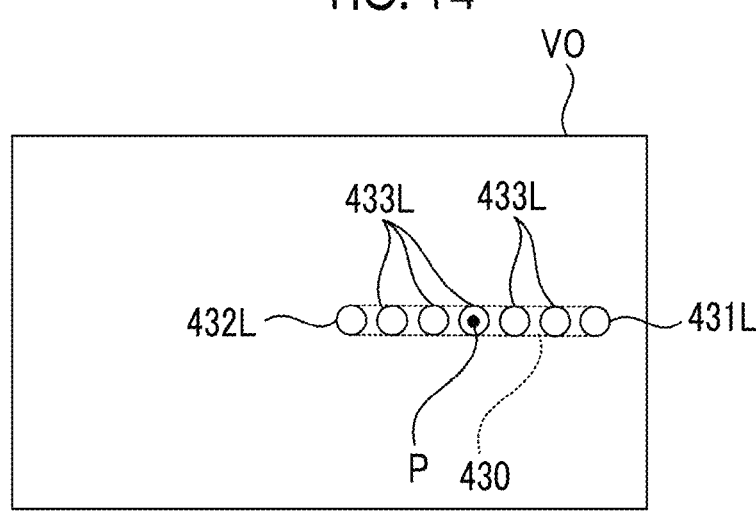
FIG. 14 is a view showing a modification example of an irradiation form of a plurality of point-like light beams.
Figure 14:
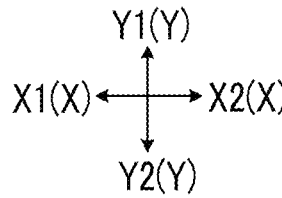

In the description made hereinbefore, it is assumed that two point-like light beams including the light 431L and the light 432L are emitted from the distal end part 40. However, the number of point-like light beams to be emitted is not limited to two and may be three or more. For example, as shown in FIG. 14, a light emitting unit may be added to the distal end part 40 so that at least one (five in the example of FIG. 14) point-like light beam 433L is emitted between the light 432L and the light 431L. By increasing the number of point-like light beams, the visibility of the irradiation range 430 can be improved. In addition, it is possible to support more complicated treatments.

For example, by changing the irradiation sizes of seven light beams shown in FIG. 14 non-uniform, it is possible to easily recognize the insertion position of the treatment tool. Specifically, the light 433L overlapping the intersection P which is one of the seven point-like light beams shown in FIG. 14 is configured to have a larger irradiation size than the other light beams, so that the insertion position of the treatment tool can be easily recognized. In addition, lighting patterns of the seven light beams are controlled, for example, light is emitted from the light 431L side toward a light 432L side in turn, and emission of all the seven light beams is completed. Then, by repeating processing of stopping the emission of all the light beams (dynamically changing the seven light beams), it is possible to easily recognize which of the light 432L and the light 431L is at a position close to the ultrasound transmission/reception unit 41. By changing the brightness or the color of each of the seven light beams in turn from the direction X2 toward the direction X1, light may be dynamically changed.

Figure 15:
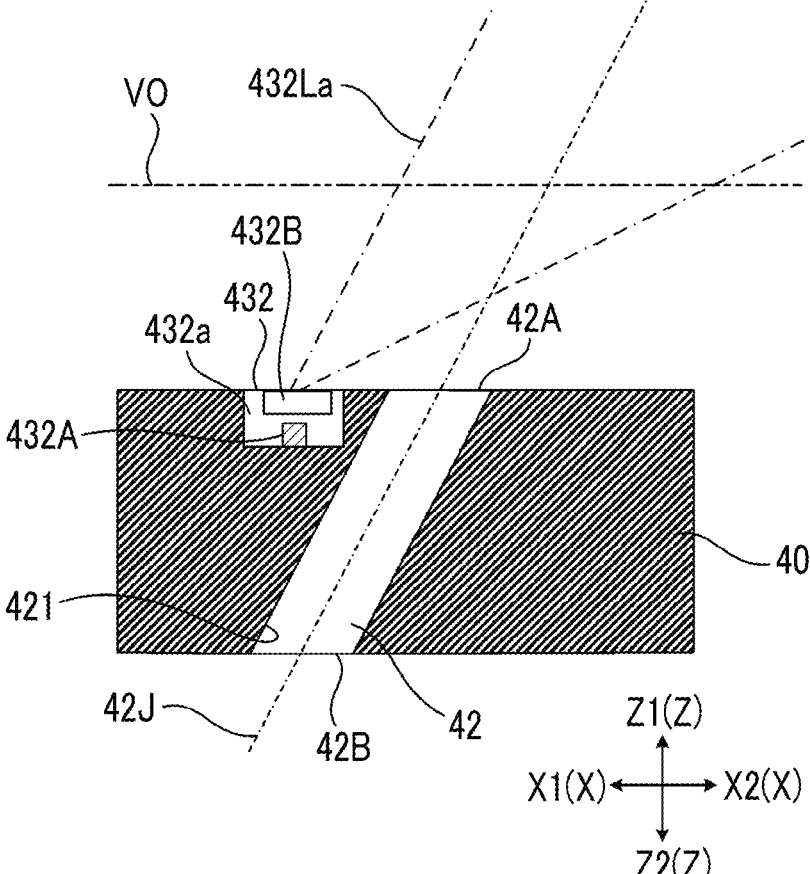
FIG. 15 is a view for describing a third modification example of the distal end part 40 and is a view corresponding to FIG. 6.
Figure 16:
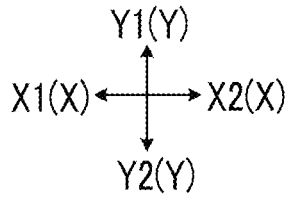
FIG. 16 is a view showing that the imaginary plane VO is irradiated with light emitted from a second light emitting unit 432.

FIG. 15 is a view for describing a third modification example of the distal end part 40 and is a view corresponding to FIG. 6. The distal end part 40 of the third modification example has the same configuration as that of the distal end part 40 shown in FIGS. 2 to 5, except that the first light emitting unit 431 is deleted and an optical path controller 432B is added to the recessed portion 432*a* of the second light emitting unit 432. FIG. 16 is a view showing that the imaginary plane VO is irradiated with light emitted from the second light emitting unit 432.

The optical path controller 432B converts light emitted from the light source 432A into linear light 432La extending along the axial direction X (the same as the arrangement direction of the ultrasound oscillators 41A) and emits the linear light 432La from the second light emitting unit 432. In addition, the light 432La is emitted in a state of intersecting the extension line 42J. As described above, the second light emitting unit 432 emits the linear light 432La based on the arrangement of the ultrasound oscillators 41A. In addition, it can be said that the second light emitting unit 432 emits the linear light 432La based on the shape of the guide unit 42 since the light 432La is emitted to overlap the extension line 42J. In addition, in a case where the configuration shown in FIGS. 10 to 13 is adopted as the guide unit 42, a direction in which the opening 42A constituting an entrance of the guide unit 42 extends and a direction in which the linear light 432La extends are the same. Also from this, it can be said that the second light emitting unit 432 emits the linear light 432La based on the shape of the guide unit 42.

Figure 17:
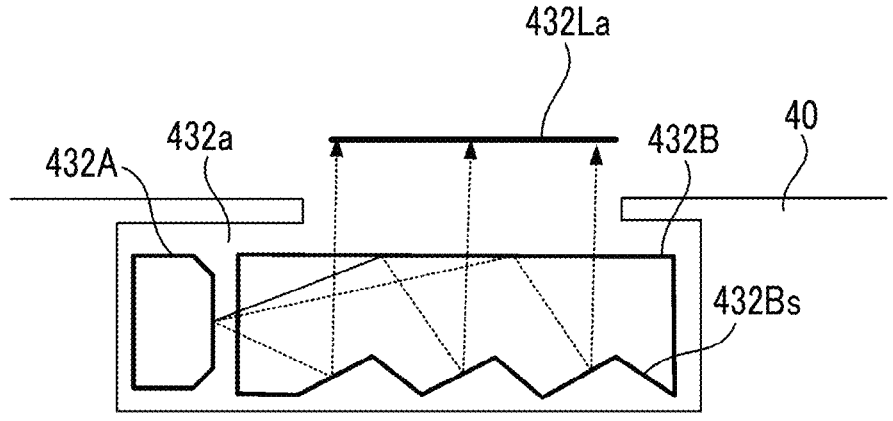
FIG. 17 is a schematic view showing a first configuration example of an optical path controller 432B.

FIG. 17 is a schematic view showing a first configuration example of the optical path controller 432B. In the example shown in FIG. 17, the light source 432A and the optical path controller 432B are disposed in the recessed portion 432a to be arranged along a bottom surface of the recessed portion 432a. The optical path controller 432B is an optical member composed of glass, a resin, or the like that generates the linear light 432La as a mountain-shaped reflecting surface 432Bs reflecting light incident into the inside in a direction intersecting the emission direction of light from the light source 432A. The optical path controller 432B can also be replaced with a micro electro mechanical systems (MEMS) mirror, a rotating mirror of a polyhedron, or the like.

Figures 18, 19, 20:
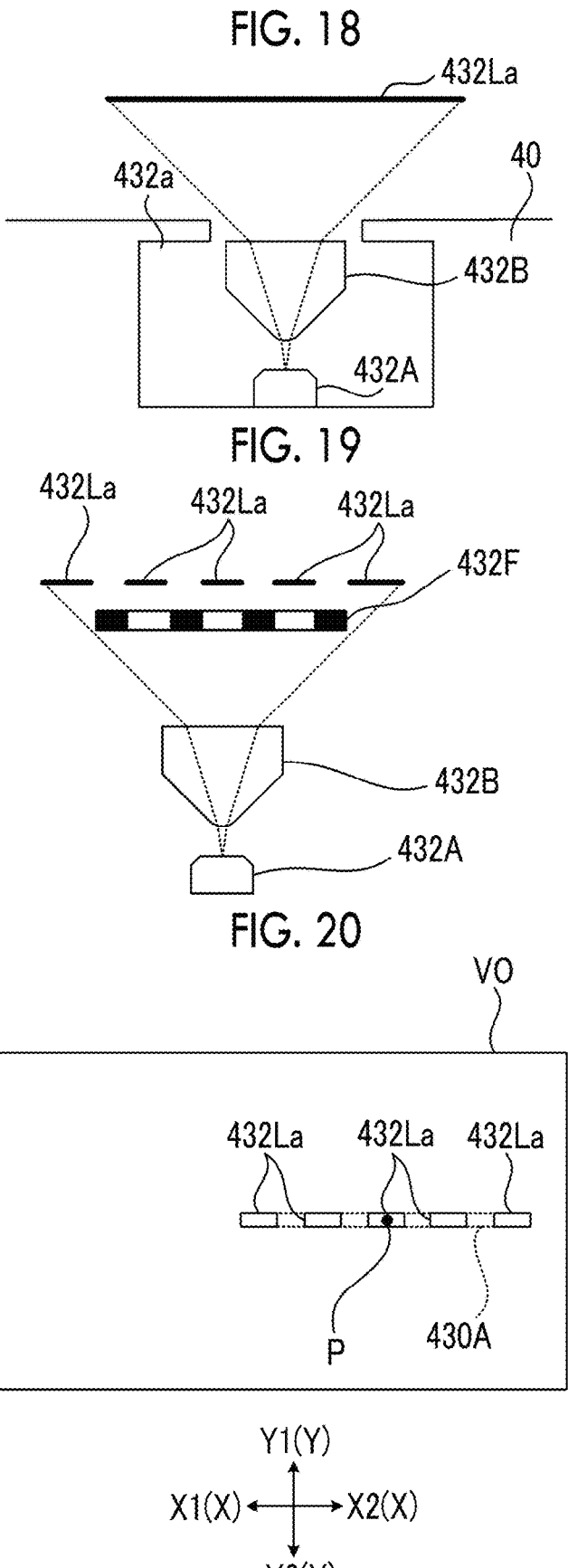
FIG. 18 is a schematic view showing a second configuration example of the optical path controller 432B.
FIG. 19 is a view showing a modification example of a light emission form of a plurality of linear light beams.
FIG. 20 is a view showing that the imaginary plane VO is irradiated with light from the second light emitting unit 432 having the configuration shown in FIG. 19.

FIG. 18 is a schematic view showing a second configuration example of the optical path controller 432B. In the example shown in FIG. 18, the light source 432A and the optical path controller 432B are disposed in the recessed portion 432a to be arranged in a direction perpendicular to the bottom surface of the recessed portion 432a. The optical path controller 432B is composed of a Powell lens and converts incident light into the linear light 432La to emit the light 432La from an opening surface of the recessed portion 432a. The optical path controller 432B can also be replaced with a cylindrical lens.

As described above, with the distal end part 40 of the third modification example, since the direction in which the light 432La shown in FIG. 16 extends can be recognized as the direction of insertion of the treatment tool, a treatment with the treatment tool with respect to a part against which the ultrasound transmission/reception unit 41 is pressed can be efficiently performed as in the configuration shown in FIGS. 2 to 5. Among the linear light 432La, light at an end edge on the direction X1 side in FIG. 15 may be configured to be emitted in the direction along the inner wall surface 421.

It is preferable to devise a method for making it easy to recognize which of both ends of the light 432La shown in FIG. 16 is closer to the ultrasound transmission/reception unit 41 in the distal end part 40 of the third modification example. For example, the light 432La may be configured such that a plurality of colors are arranged in the direction in which the light 432La extends. For example, a color filter in which a plurality of color filters are disposed in a one-dimensional shape may be disposed above the optical path controller 432B in FIG. 17 or above the optical path controller 432B in FIG. 18 to realize the above configuration.

The second light emitting unit 432 may be configured to emit a plurality of linear light beams 432La instead of emitting the single linear light beam 432La. For example, as shown in FIG. 19, a light shielding filter 432F having a partially light shielding region is disposed on a light emitting side of the optical path controller 432B composed of the Powell lens, so that the plurality of (five in the example of FIG. 19) linear light beams 432La arranged at intervals in the axial direction X may be emitted.

FIG. 20 is a view showing that the imaginary plane VO is irradiated with light from the second light emitting unit 432 having the configuration shown in FIG. 19. As shown in FIG. 20, the imaginary plane VO is irradiated in a state where the five linear light beams 432La are arranged at intervals along the axial direction X. In the five linear light beams 432La shown in FIG. 20, by changing the color of a specific light beam 432La, dynamically changing each light beam 432La, or changing the width of the specific light 432La in the direction X or the direction Y, it is possible to recognize a direction in which the ultrasound transmission/reception unit 41 is present or the position of the guide unit.

Figures 21, 22:
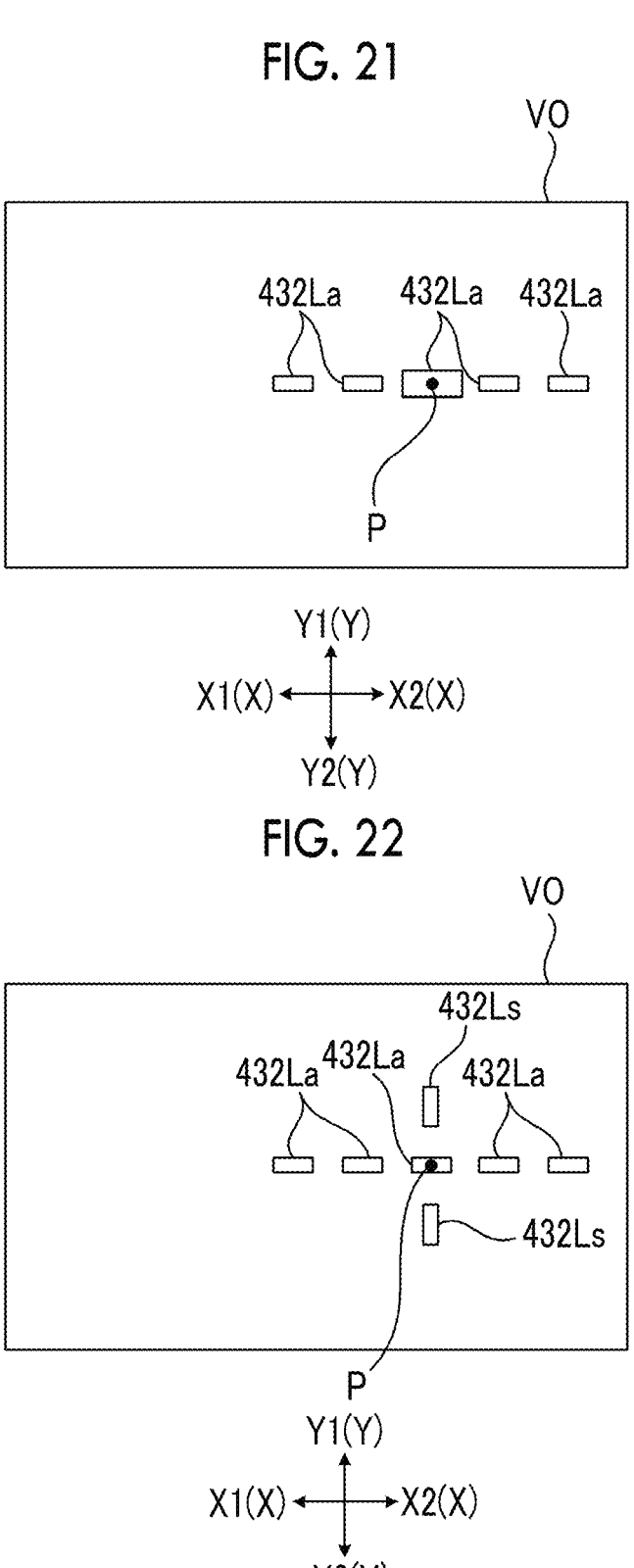
FIG. 21 is a view showing a modification example of an irradiation form of the light shown in FIG. 20.
FIG. 22 is a view showing another modification example of an irradiation form of the light shown in FIG. 20.

The position of the intersection P in the irradiation range 430A of the five linear light beams 432La shown in FIG. 20 can be changed in a right-left direction in the drawing depending on a position where the imaginary plane VO is disposed in the direction Z, but it is preferable that the five linear light beams 432La are emitted such that the middle light 432La of the five light beams 432La and the intersection P overlap each other at all times. As a result, the insertion position of the treatment tool with respect to the irradiation range 430A can be easily recognized. In such a case, as shown in FIG. 21, for the light 432La overlapping the intersection P, at least one (defined as an irradiation width of the light 432La) of the width in the direction Y or the width in the direction X is made different from the other light beams 432La (for example, is made larger as in FIG. 21), so that the insertion position of the treatment tool can be more easily recognized. For the irradiation widths of the five light beams 432La, the irradiation width of the light 432La that overlaps the intersection P may be set to be the maximum, and the irradiation width may be set to be smaller as the distance from the intersection P increases. As described above, by making the irradiation widths of the five light beams 432La shown in FIG. 20 non-uniform, the insertion position of the treatment tool can be easily recognized.

In addition, for the light 432La overlapping the intersection P, a color thereof is set to a color different from those of the other light beams 432La, so that the insertion position of the treatment tool can be more easily recognized. In addition, for the light 432La overlapping the intersection P, brightness thereof is set to brightness different from those of the other light beams 432La, so that the insertion position of the treatment tool can be more easily recognized. In addition, by intermittently emitting the light 432La overlapping the intersection P and continuously emitting the other light beams 432La, the insertion position of the treatment tool can be more easily recognized.

Up to here, it is assumed that the plurality of linear light beams 432La are emitted from the distal end part 40 in a state of being arranged in the axial direction X. For example, as shown in FIG. 22, a light emitting unit may be added to the distal end part 40 so as to emit a plurality of (two in the example of FIG. 22) linear light beams 432Ls arranged in a direction intersecting (orthogonal in the example of FIG. 22) a direction in which the five light beams 432La are arranged, in addition to the five light beams 432La shown in FIG. 20.

The distal end part 40 shown in FIGS. 2 to 14 comprises a light emitting unit that emits a plurality of point-like light beams arranged in one direction (that is, a linear shape). As a modification example, a configuration where the distal end part 40 is provided with a light emitting unit that emits a plurality of point-like light beams arranged in an annular shape may be adopted.

Figures 23, 24:
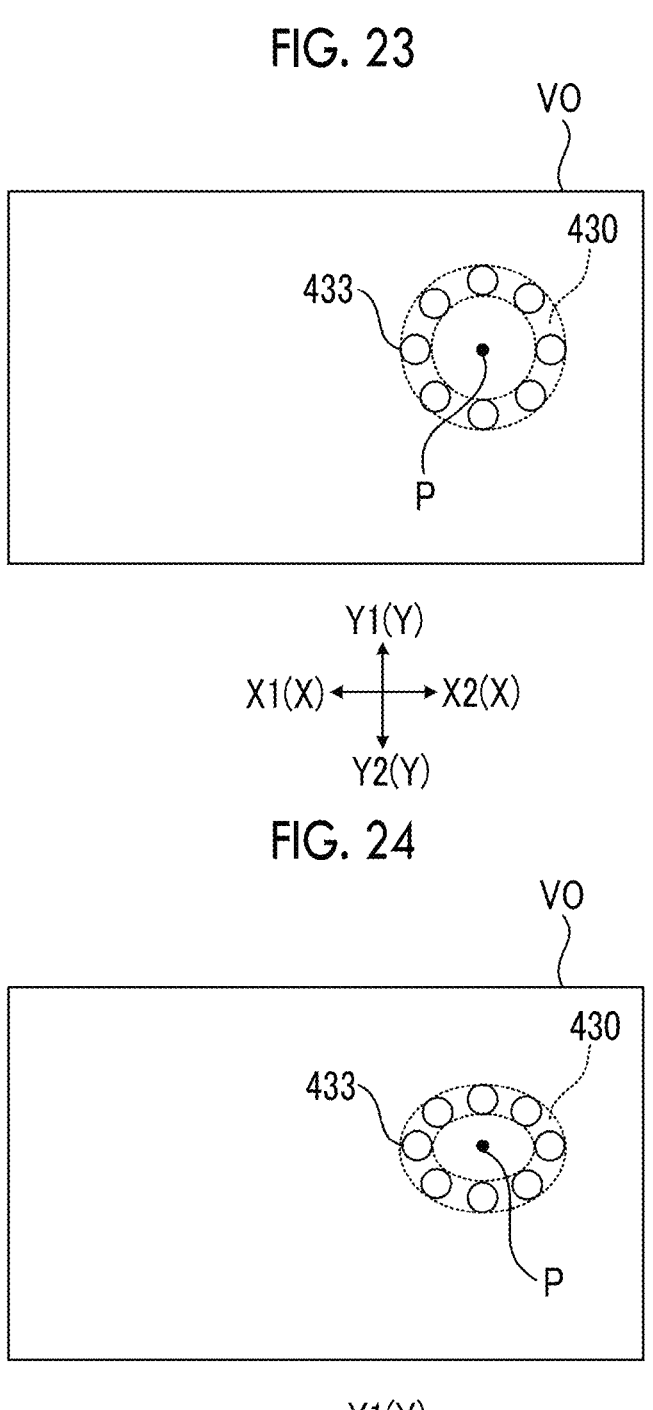
FIG. 23 is a view showing a state where the imaginary plane VO is irradiated with light in a case where the distal end part 40 is provided with a light emitting unit that emits a plurality of point-like light beams arranged in a perfect circle.
FIG. 24 is a view showing a state where the imaginary plane VO is irradiated with light in a case where the distal end part 40 is provided with a light emitting unit that emits a plurality of point-like light beams arranged in an elliptical shape.

FIG. 23 is a view showing a state where the imaginary plane VO is irradiated with light in a case where the distal end part 40 is provided with a light emitting unit that emits a plurality of point-like light beams arranged in a cyclic shape. In the example shown in FIG. 23, the imaginary plane VO is irradiated with eight point-like light beams 433 in a state of being arranged in a perfect circle. The extension line 42J intersects inside the irradiation range 430 of the eight point-like light beams 433, and the intersection P is positioned inside the irradiation range 430. With this configuration, the treatment tool can easily reach the guide unit 42 by inserting the treatment tool while targeting the inside of the irradiation range 430.

For example, the eight light beams 433 shown in FIG. 23 can be realized by disposing eight light emitting units in an annular shape around the opening 42A and emitting point-like light in a direction along the extension line 42J from each light emitting unit.

In the configuration shown in FIG. 23, the imaginary plane VO is irradiated in a state where the eight point-like light beams 433 are arranged in a perfect circle, but the present invention is not limited thereto. For example, as shown in FIG. 24, the imaginary plane VO may be irradiated in a state where the eight point-like light beams 433 are arranged in an elliptical shape. In the example of FIG. 24, an outer edge of the irradiation range 430 has an elliptical shape, a major axis direction thereof matches the axial direction X, and a minor axis direction thereof matches the direction Y. With this configuration, the treatment tool can easily reach the guide unit 42 by inserting the treatment tool while targeting the inside of the irradiation range 430. In addition, since the major axis direction of the irradiation range 430 matches the axial direction X, the direction of insertion of the treatment tool can be easily recognized depending on the shape of the irradiation range 430.

The same effect can be obtained even in a case where the distal end part 40 is provided with a light emitting unit that irradiates the entire irradiation range 430 having a perfect annular shape shown in FIG. 22 with light or the distal end part 40 is provided with a light emitting unit that irradiates the entire irradiation range 430 having an elliptical annular shape shown in FIG. 23 with light. Since such perfect annular or elliptical annular light corresponds to superposition of both ends of curved light, it can be said that the perfect annular or elliptical annular light is one linear light beam. Such annular and linear light beams can be generated, for example, by shielding a central portion of point-like light having a large irradiation size.

The ultrasound probe 1 that has been described hereinbefore has the guide unit 42, but the guide unit 42 is not essential and can be omitted. Even in a case where the ultrasound probe 1 that does not include the guide unit 42 is used, the arrangement direction of the ultrasound oscillators 41A inserted into the subject from the outside of the subject can be easily recognized by irradiating the abdominal wall with the plurality of point-like light beams or at least one linear light beam shown in FIGS. 7, 14, 16, 20, 21, 22, 24, and the like.

For example, in some cases, it is desired to check a part through an ultrasound image by making the arrangement direction of the ultrasound oscillators 41A match a direction orthogonal to the spine of the subject. In such a case, it is possible to easily recognize what is the arrangement direction of the ultrasound oscillators 41A with respect to the spine based on a direction in which the plurality of point-like light beams irradiating the abdominal wall are arranged or a direction in which linear light extends (in the example of FIG. 24, the major axis direction of the irradiation range 430). As a result, it is possible to efficiently perform the intended examination.

Figure 25:
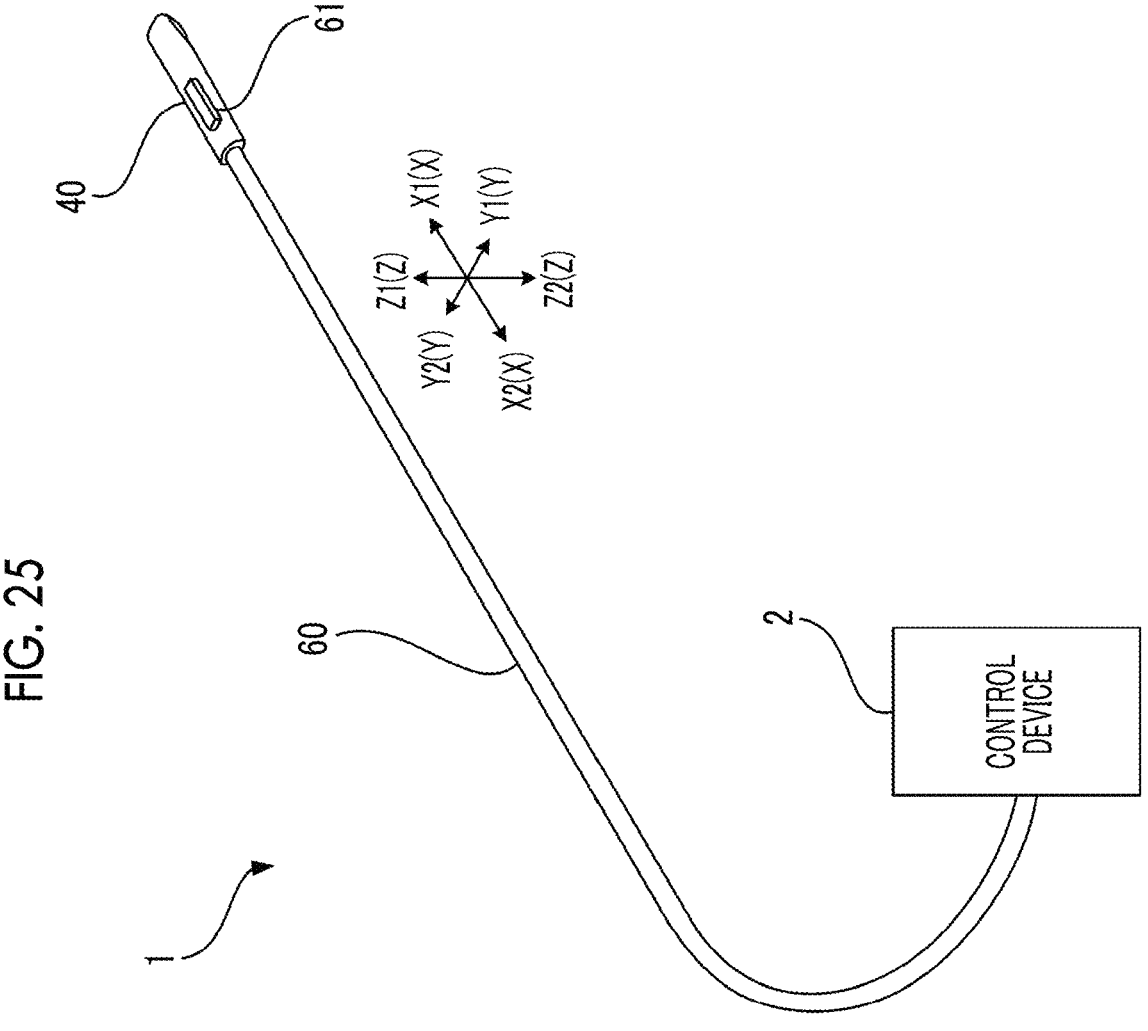
FIG. 25 is a view showing a modification example of the ultrasound probe 1.

The ultrasound probe 1 may be a drop-in type probe (see FIG. 25) that does not have a support mechanism that can hold the position of the distal end part 40 and that is moved or fixed by gripping forceps or the like. The drop-in type ultrasound probe 1 shown in FIG. 25 has a configuration where a cable 60 having lower stiffness and flexibility than those of the distal end part 40 is provided at the proximal end of the distal end part 40, and a proximal end of the cable 60 is connected to the control device 2. Such a drop-in type ultrasound probe 1 can be moved in a wide range by gripping a grip unit 61 provided at the distal end part 40 using forceps or the like inserted from a trocar different from the trocar into which the ultrasound probe 1 is inserted.

It is preferable that the ultrasound probe 1 is configured to emit light from the light emitting unit in a state where the distal end part 40 is inserted into the subject and not to emit light from the light emitting unit in a state where the distal end part 40 is outside the subject.

For example, in a case where the control device 2 generates an ultrasound image based on the output of the ultrasound probe 1, displays the ultrasound image on the display, and receives a light emission instruction from the user, the control device 2 causes the light emitting unit to emit light. Alternatively, the control device 2 detects the brightness of the environment in which the ultrasound diagnostic apparatus 100 is placed and causes the light emitting unit to emit light in a case where the detected brightness is equal to or less than a threshold value. In a situation where the insertion part 10 is inserted into the subject, the brightness is likely to be equal to or less than the threshold value. Therefore, in a state where the distal end part 40 is outside the subject, light can be prevented from being emitted from the light emitting unit. Alternatively, the control device 2 may acquire an image captured by the endoscope inserted into the trocar and may cause the light emitting unit to emit light in a case where it is determined that the image includes at least a part of the insertion part 10 of the ultrasound probe 1. The determination as to whether or not the ultrasound probe 1 is included in the image of the endoscope may be performed by a processor device connected to the endoscope, instead of the control device 2, and the control device 2 may be configured to acquire the determination result from the processor device.

As described hereinbefore, at least the following matters are described in the present specification. In the following, components corresponding to the embodiment are shown in parentheses, but the present invention is not limited thereto.

(1)
An ultrasound probe (ultrasound probe 1) comprising:
a distal end part (distal end part 40) that is provided with an ultrasound oscillator (ultrasound oscillator 41A); and
a light emitting unit (first light emitting unit 431 and second light emitting unit 432) that is provided at the distal end part and that emits light toward an opposite side to a side where the ultrasound oscillator is provided,
in which the light emitting unit emits a plurality of point-like light beams (light 431L and light 432L) or linear light (light 432La).

(2)
The ultrasound probe according to (1), further comprising:
a guide unit (guide unit 42) that is provided at the distal end part and that guides a treatment tool,
in which the light emitting unit emits the plurality of point-like light beams or the linear light based on a shape of the guide unit.

(3)
The ultrasound probe according to (2),
in which the guide unit is composed of a hole portion formed in the distal end part, and
light emitted by the light emitting unit includes light emitted in a direction along an inner wall surface of the hole portion.

(4)

The ultrasound probe according to (2), in which a subject is irradiated with the plurality of point-like light beams emitted from the light emitting unit in a state of being arranged in one direction, the guide unit is composed of a hole portion formed in the distal end part, and an emission direction of the point-like light is inclined to an extension line side with respect to a direction in which an extension line of an axial line (extension line 42J) of the hole portion extends.

(5)

The ultrasound probe according to (2), in which the guide unit is composed of a hole portion formed in the distal end part, a subject is irradiated with the plurality of point-like light beams emitted from the light emitting unit in a state of being arranged in an annular shape or the subject is irradiated with the linear light emitted from the light emitting unit in an annular state, and an extension line (extension line 42J) of an axial line of the hole portion intersects an inside of the annular light which irradiates the subject.

(6)

The ultrasound probe according to any one of (1) to (5), in which a subject is irradiated with the plurality of point-like light beams emitted from the light emitting unit in a state of being arranged in annular shape or the subject is irradiated with the linear light emitted from the light emitting unit in an annular state.

(7)

The ultrasound probe according to (6), in which the annular shape is an elliptical shape or a perfect circle.

(8)

The ultrasound probe according to any one of (2) to (4), in which the light emitting unit includes a first light emitting unit and a second light emitting unit provided at positions facing each other with the guide unit interposed therebetween.

(9)

The ultrasound probe according to (8), in which a first distance (first distance L1) between the first light emitting unit and the guide unit and a second distance (second distance L2) between the second light emitting unit and the guide unit are different from each other.

(10)

The ultrasound probe according to (9), in which the second light emitting unit is provided on a distal end side of the distal end part with respect to the first light emitting unit, and the second distance is larger than the first distance.

(11)

The ultrasound probe according to any one of (1) to (10), in which the light emitting unit emits the plurality of point-like light beams or the linear light based on arrangement of the ultrasound oscillator at the distal end part.

(12)

The ultrasound probe according to (11), in which the light emitting unit emits the plurality of point-like light beams arranged along an arrangement direction of the ultrasound oscillator or the linear light extending along the arrangement direction of the ultrasound oscillator.

(13)

The ultrasound probe according to any one of (1) to (12), in which the light emitting unit includes a plurality of light sources.

(14)

The ultrasound probe according to (13), in which the plurality of light sources generate different colors.

(15)

The ultrasound probe according to any one of (1) to (14), in which the light emitting unit emits laser light.

(16)

The ultrasound probe according to any one of (1) to (15), in which a subject is irradiated with the plurality of point-like light beams in a state of being arranged at an interval.

(17)

The ultrasound probe according to any one of (1) to (16), in which the light emitting unit emits a plurality of the linear light beams arranged in one direction, and a subject is irradiated with the plurality of linear light beams in a state of being arranged at an interval.

(18)

The ultrasound probe according to any one of (1) to (17), in which irradiation sizes of the plurality of point-like light beams or an irradiation width of the linear light is non-uniform.

(19)

The ultrasound probe according to (18), in which the irradiation sizes of the plurality of point-like light beams or the irradiation width of the linear light is larger in a part of a range irradiated with light than in other portions.

(20)

The ultrasound probe according to any one of (1) to (19), in which the light emitting unit emits a plurality of the linear light beams (light 432Ls, light 432La) intersecting each other.

(21)

The ultrasound probe according to any one of (1) to (20), in which the light emitting unit dynamically changes the light.

EXPLANATION OF REFERENCES

1: ultrasound probe
X: axial direction
Y, Z: direction
L1: first distance
2: control device
L2: second distance
10: insertion part
20: connecting portion
30: bendable part
40: distal end part
41: ultrasound transmission/reception unit
41A: ultrasound oscillator
41B: scan range
42: guide unit
42J, 42L, 42R: extension line
42A, 42B: opening
42C: through-hole
45: scale
45A: mark
50: operating part
60: cable
100: ultrasound diagnostic apparatus
100J: axial line 421, 422: inner wall surface
430, 430A: irradiation range
431: first light emitting unit
431A, 432A: light source
431L, 432L, 432La, 432Ls, 433, 433L: light
431a, 432a: recessed portion
432: second light emitting unit
432B: optical path controller
432F: light shielding filter
432Bs: reflecting surface

What is claimed is:

1. An ultrasound probe comprising:
a distal end part that is provided with an ultrasound oscillator;
a light emitting unit that is provided at the distal end part and that emits light toward an opposite side to a side where the ultrasound oscillator is provided, wherein the light emitting unit emits a plurality of light beams or linear light; and
a guide unit that is provided at the distal end part and that guides a treatment tool,
wherein the light emitting unit includes a first light emitting unit and a second light emitting unit provided at positions facing each other with the guide unit interposed therebetween,
wherein a first distance between the first light emitting unit and the guide unit and a second distance between the second light emitting unit and the guide unit are different from each other.

2. The ultrasound probe according to claim 1,
wherein the light emitting unit emits the plurality of light beams that are based on a shape of the guide unit or the linear light that is based on the shape of the guide unit.

3. The ultrasound probe according to claim 2,
wherein the guide unit is composed of a hole portion formed in the distal end part, and
light emitted by the light emitting unit includes light emitted in a direction along an inner wall surface of the hole portion.

4. The ultrasound probe according to claim 2,
wherein a subject is irradiated with the plurality of light beams emitted from the light emitting unit in a state of being arranged in one direction,
the guide unit is composed of a hole portion formed in the distal end part, and
an emission direction of the light is inclined to an extension line side with respect to a direction in which an extension line of an axial line of the hole portion extends.

5. The ultrasound probe according to claim 2,
wherein the guide unit is composed of a hole portion formed in the distal end part,
a subject is irradiated with the plurality of light beams emitted from the light emitting unit in a state of being arranged in an annular shape or the subject is irradiated with the linear light emitted from the light emitting unit in an annular state, and an extension line of an axial line of the hole portion intersects an inside of the annular light which irradiates the subject.

6. The ultrasound probe according to claim 1,
wherein a subject is irradiated with the plurality of light beams emitted from the light emitting unit in a state of being arranged in an annular shape or the subject is irradiated with the linear light emitted from the light emitting unit in an annular state.

7. The ultrasound probe according to claim 6,
wherein the annular shape is an elliptical shape or a perfect circle.

8. The ultrasound probe according to claim 2,
wherein the second light emitting unit is provided on a distal end side of the distal end part with respect to the first light emitting unit, and
the second distance is larger than the first distance.

9. The ultrasound probe according to claim 1,
wherein the light emitting unit emits the plurality of light beams or the linear light based on arrangement of the ultrasound oscillator at the distal end part.

10. The ultrasound probe according to claim 9,
wherein the light emitting unit emits the plurality of light beams arranged along an arrangement direction of the ultrasound oscillator or the linear light extending along the arrangement direction of the ultrasound oscillator.

11. The ultrasound probe according to claim 1,
wherein the light emitting unit includes a plurality of light sources.

12. The ultrasound probe according to claim 11,
wherein the plurality of light sources generate different colors.

13. The ultrasound probe according to claim 1,
wherein the light emitting unit emits laser light.

14. The ultrasound probe according to claim 1,
wherein a subject is irradiated with the plurality of light beams in a state of being arranged at an interval.

15. The ultrasound probe according to claim 1,
wherein the light emitting unit emits a plurality of the linear light beams arranged in one direction, and
a subject is irradiated with the plurality of linear light beams in a state of being arranged at an interval.

16. The ultrasound probe according to claim 1,
wherein irradiation sizes of the plurality of light beams or an irradiation width of the linear light is non-uniform.

17. The ultrasound probe according to claim 16,
wherein the irradiation sizes of the plurality of light beams or the irradiation width of the linear light is larger in a part of a range irradiated with light than in other portions.

18. The ultrasound probe according to claim 1,
wherein the light emitting unit emits a plurality of the linear light beams intersecting each other.

19. The ultrasound probe according to claim 1,
wherein the light emitting unit dynamically changes the light.

* * * * *